United States Patent
Anklesaria

(10) Patent No.: US 8,938,859 B1
(45) Date of Patent: Jan. 27, 2015

(54) DEVICE WITH FASTENING ASSEMBLY

(71) Applicant: Kaiomars P. Anklesaria, Bloomingdale, GA (US)

(72) Inventor: Kaiomars P. Anklesaria, Bloomingdale, GA (US)

(73) Assignee: Enuresis Solutions LLC, Savannah, GA (US)

( * ) Notice: Subject to any disclaimer, the term of this patent is extended or adjusted under 35 U.S.C. 154(b) by 175 days.

(21) Appl. No.: 13/674,232

(22) Filed: Nov. 12, 2012

(51) Int. Cl.
*A45F 5/02* (2006.01)

(52) U.S. Cl.
CPC . *A45F 5/02* (2013.01); *Y10S 224/93* (2013.01)
USPC ............. 24/3.12; 24/3.11; 224/255; 224/668; 224/930

(58) Field of Classification Search
CPC .............. A45F 5/02; A45F 5/00; A45F 5/021
USPC .......... 24/3.12, 3.11, 380, 377; 224/255, 668, 224/930
See application file for complete search history.

(56) References Cited

U.S. PATENT DOCUMENTS

| 5,261,122 A | * | 11/1993 | Otsuki et al. | 455/351 |
| 2007/0178761 A1 | * | 8/2007 | Wemmer | 439/596 |

* cited by examiner

*Primary Examiner* — Jack W Lavinder
(74) *Attorney, Agent, or Firm* — G. Brian Pingel; David M. Breiner

(57) ABSTRACT

Disclosed is an assembly. The assembly may be comprised of a device having a first engaging member, a second member having a second engaging member engaging the first engaging member, and a third member locked in place by the first engaging member and the second engaging member. The first and second members together can serve as an attachment device. The third member, held in place by the first and second engaging members, can serve as an attachment.

5 Claims, 12 Drawing Sheets

DEVICE WITH FASTENING ASSEMBLY

BACKGROUND

1. Field

Example embodiments are directed to an assembly having a device and members for fastening the device to a target. In example embodiments, the assembly may include at least one fastener that may be usable for fastening the device, for example, an alarm, to a target, for example, an article of clothing.

2. Description of the Related Art

Nocturnal enuresis, also known as bed-wetting, is a relatively common event for young children. Although most children outgrow nocturnal enuresis by the age of 6 or 7, some children continue to experience nocturnal enuresis for several years thereafter. Some adults also continue to experience this condition.

FIG. 1 is a view of a detection system 10 usable for detecting enuresis. As shown in FIG. 1, the system 10 includes a sensor 20, a cable 25, and an alarm 30. In use, the sensor 20 is positioned inside or near a child's undergarment 15 and the alarm 30 is attached to a shirt or pajama top by a safety pin 35 (see FIG. 2). The alarm 30 is typically configured to either vibrate or produce a sound in the event the sensor 20 detects urine. This device could also transmit a signal wirelessly to a receiver which actually serves as an alarm. Thus, a child wearing the system 10 may be awakened during a bed wetting event. The system 10, accordingly, allows the child an opportunity to wake up and change his/her cloths in order to avoid sleeping in a urine soaked undergarment.

FIG. 2 is a back-side view of the alarm 30. As shown in FIG. 2, the alarm 30 is enclosed in a case which includes a tunnel like protrusion 32 through which a portion of the safety pin 35 passes. The safety pin 35 is captured by the tunnel like protrusion 32 and is therefore not removable from the case. In the event the tunnel like protrusion 32 breaks, the safety pin 35 is no longer usable for attaching the alarm 30 to the child's clothing.

SUMMARY

Example embodiments are directed to an assembly having a device and members for fastening the device to a target. In example embodiments the assembly may include at least one fastener that may be usable for fastening the device, for example, an alarm, to a target, for example, an article of clothing.

In accordance with example embodiments, an assembly may include a first engaging member on a device, a second engaging member engaging the first engaging member, and a first fastener configured to attach the device to a target, wherein the first fastener is captured by the first engaging member and the second engaging member. A second fastener could also be held in place between the first and second members above, and serve as another fastening device.

BRIEF DESCRIPTION OF THE DRAWINGS

Example embodiments are described in detail below with reference to the attached drawing figures, wherein.

DETAILED DESCRIPTION

Figure 1:
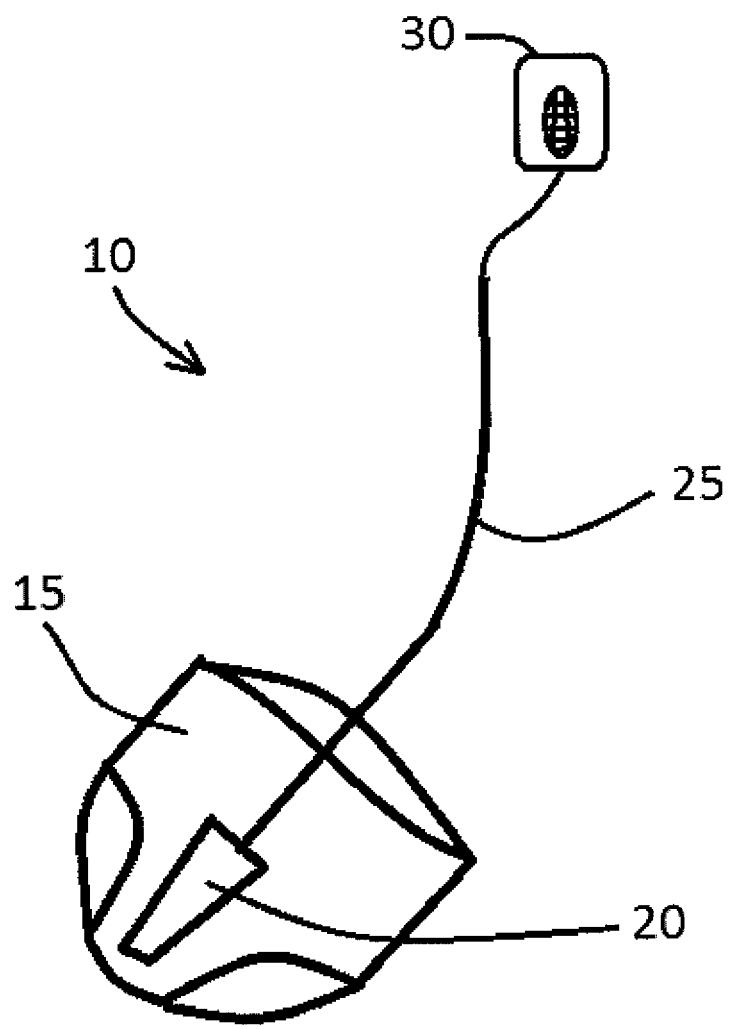
FIG. 1 is a view of a conventional system used for detecting a bed wetting event.
Figure 2:
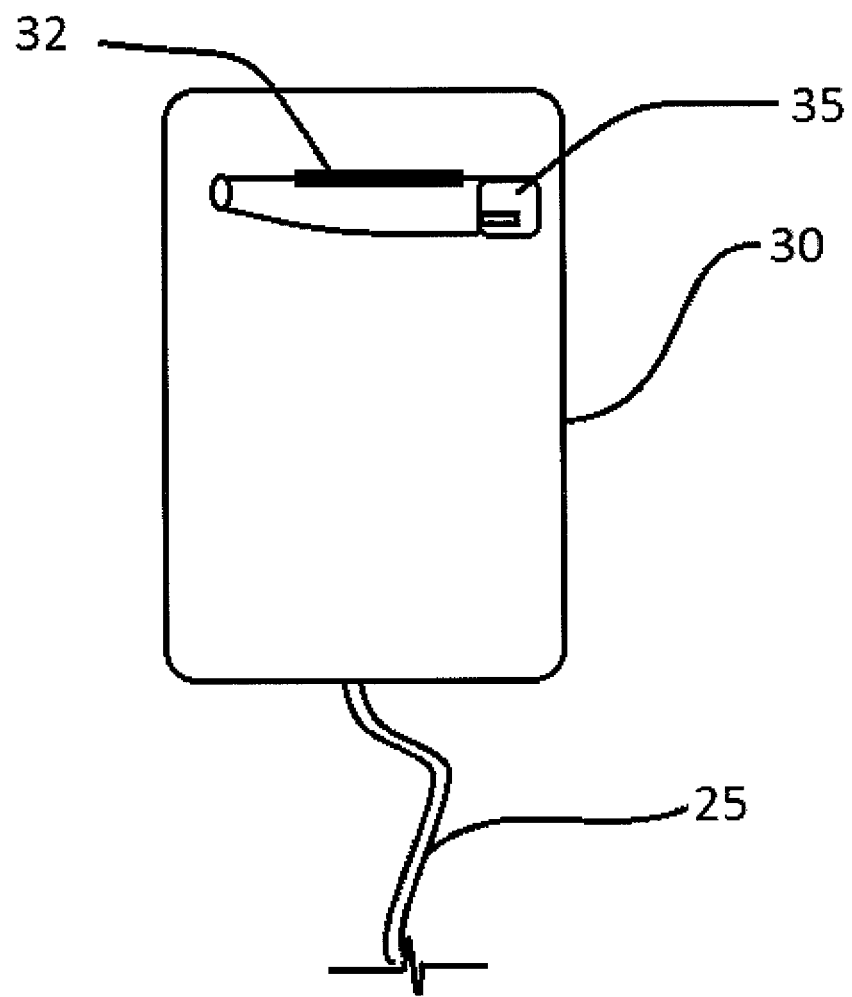
FIG. 2 is a view of a conventional alarm used in the conventional system for detecting a bed wetting event.

Example embodiments of the invention will now be described with reference to the accompanying drawings. Example embodiments, however, should not be construed as limiting the invention since the invention may be embodied in different forms. Example embodiments illustrated in the figures are provided so that this disclosure will be thorough and complete. In the drawings, the sizes of components may be exaggerated for clarity.

In this application, when an element is referred to as being "on," "attached to," "connected to," or "coupled to" another element, it can be directly on, attached to, connected to, or coupled to the other element or intervening elements that may be present. On the other hand, when an element is referred to as being "directly on," "directly attached to," "directly connected to," or "directly coupled to" another element, there are no intervening elements present. As used herein, the term "and/or" includes any and all combinations of one or more of the associated listed items.

In this application, the terms first, second, etc. are used to describe various elements, components, regions, layers, and/or sections. However, these elements, components, regions, layers, and/or sections should not be limited by these terms since these terms are only used to distinguish one element, component, region, layer, and/or section from other elements, components, regions, layers, and/or sections that may be present. For example, a first element, component region, layer or section discussed below could be termed a second element, component, region, layer, or section.

In this application, spatial terms, such as "beneath," "below," "lower," "over," "above," and "upper" (and the like) are used for ease of description to describe one element or feature's relationship to another element(s) or feature(s). The invention, however, is not intended to be limited by the spatial terms. For example, if an example of the invention illustrated in the figures is turned over, elements described as "over" or "above" other elements or features would then be oriented "under" or "below" the other elements or features. Thus, the spatial term "over" may encompass both an orientation of above and below. The device may be otherwise oriented (for example, rotated 45 degrees, 90 degrees, 180 degrees, or at other orientations) and the spatially relative descriptors used herein interpreted accordingly. The terms "conductive" and "non-conductive" relate to the conduction of electricity (a conductor) or the non conduction of electricity (an insulator).

In this application, example embodiments may be described by referring to plan views and/or cross-sectional views which may be ideal schematic views. However, it is understood the views may be modified depending on manufacturing technologies and/or tolerances. Accordingly, the invention is not limited by the examples illustrated in the views, but may include modifications in configurations formed on the basis of manufacturing process. Therefore, regions illustrated in the figures are schematic and exemplary and do not limit the invention.

The subject matter of example embodiments, as disclosed herein, is described with specificity to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other technologies. Generally, example embodiments are directed to an assembly having a device and members for fastening the device to a target. In example embodiments the assembly may include at least one fastener that may be usable for fastening the device, for example, an alarm, to a target, for example, an article of clothing.

Figure 3A:
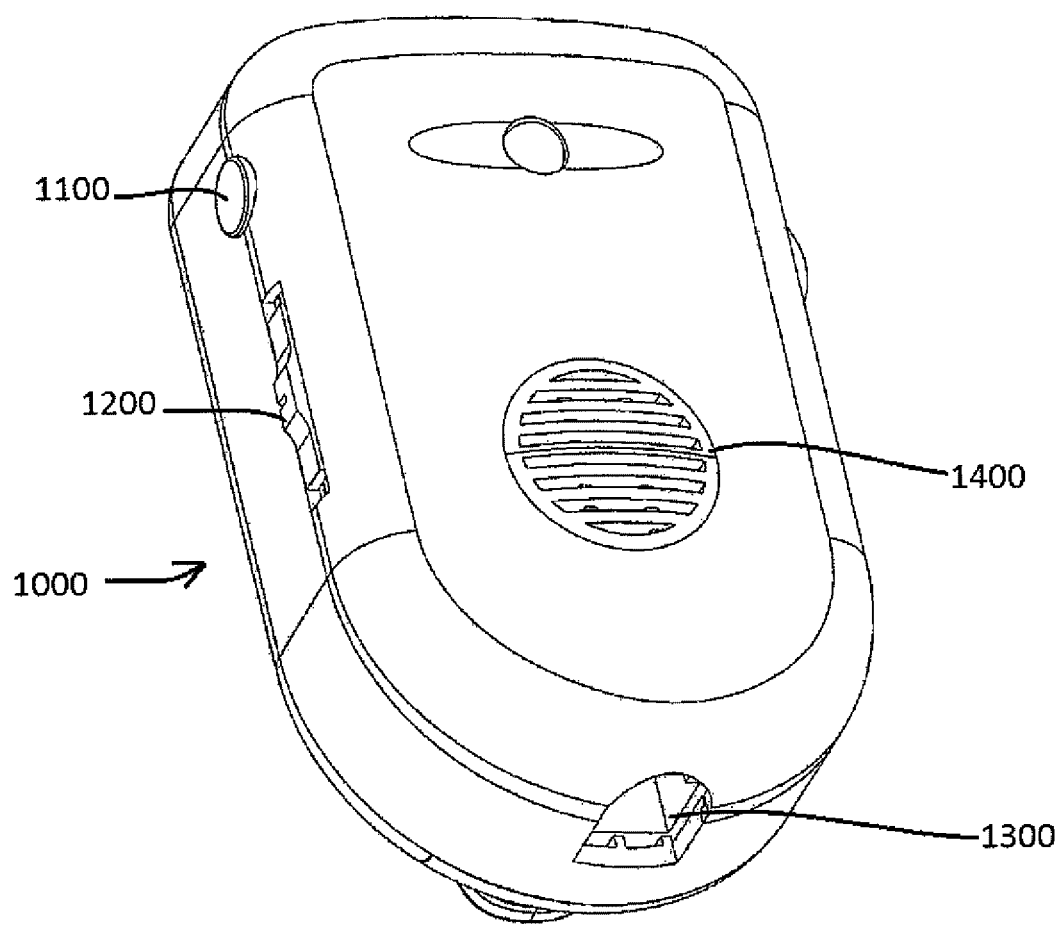
FIGS. 3A and 3B are views of an assembly in accordance with example embodiments.
Figure 3B:
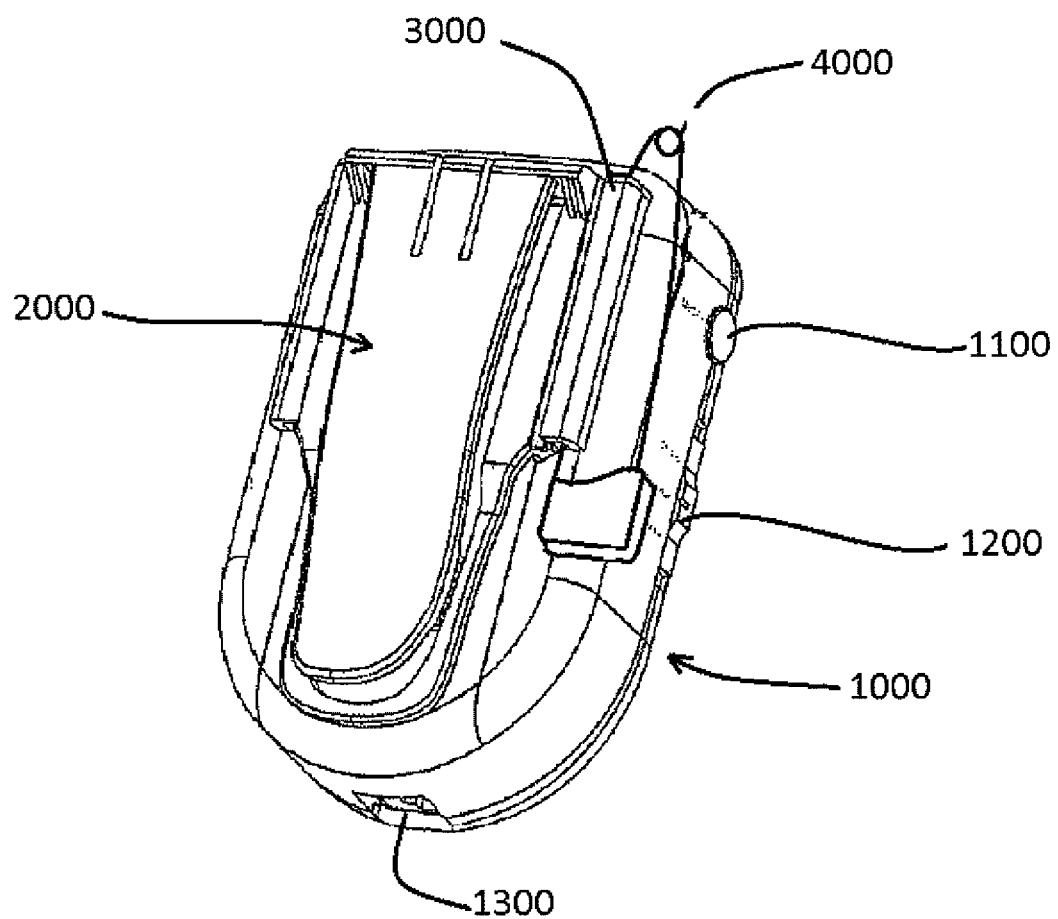

FIGS. 3A and 3B illustrate a front isometric view and a back isometric view of an assembly in accordance with example embodiments. As shown in FIGS. 3A and 3B, the assembly may include a device 1000, a first fastening member 2000, and a second fastening member 4000. In example embodiments, at least one of, or both of, the first fastening member 2000 and second fastening member 4000 may be configured to fasten the device 1000 to a target, for example, an article of clothing. In example embodiments the first and second fastening members 2000 and 4000 may be removable members wherein the first fastening member 2000 may or may not be configured to fasten the device 1000 to the target. For example, rather than being configured as a fastening member, the first fastening member 2000 may be configured to only secure the second fastening member 4000 to the device 1000.

In example embodiments, the device 1000 may be, but is not limited to, an electronic device usable with a urine detection system. For example, the device 1000 may be an alarm connected to a urine detector. In example embodiments, the alarm may be configured to at least one of vibrate and generate a noise in the event the urine detector detects urine. For example, the device 1000 may include at least one battery (not shown) to power the device 1000, a power button 1100 to turn on and off the device 1000, a switch 1200 to configure the device 1000 to at least one of vibrate and generate a sound, a speaker 1400 for generating sound, and a port 1300 into which an electrically conductive cable attached to a urine detector may be inserted.

Figure 4:
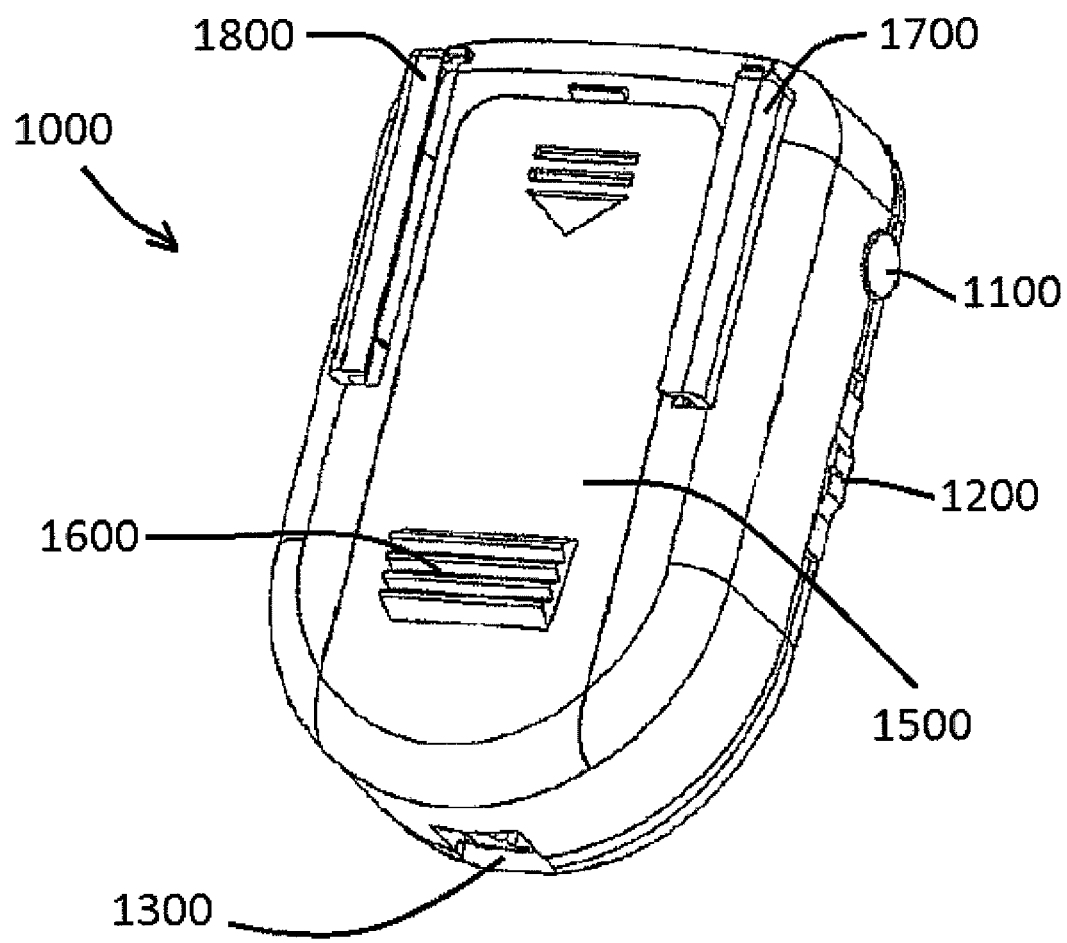
FIG. 4 is a view of a device in accordance with example embodiments.

Referring to FIG. 4, it is observed that the device 1000 may include a first engaging member 1700 and a second engaging member 1800. In example embodiments the first and second engaging members 1700 and 1800 may be formed integrally with a housing of the device 1000.

Referring to FIGS. 4, 7, and 8A-8F, the first and second engaging members 1700 and 1800 may resemble an "L" or a "C" shaped member. Thus, each of the first and second engaging members 1700 and 1800 may resemble a sleeve having a channel therein. In example embodiments, the first and second engaging members 1700 and 1800 may be configured to engage a third engaging member 2400 and a fourth engaging member 2500 (see FIGS. 5A-5F) that may be arranged on the first fastening member 2000.

In example embodiments, the third and fourth engaging members 2400 and 2500 may resemble protrusions which are insertable into the channels formed in the first and second engaging members 1700 and 1800. For example, the protrusions may resemble relatively long brick shaped members that may extend along a length of the first fastening member 2000 and may be configured to slide within the channels of the first and second engaging members 1700 and 1800. The invention, however, is not intended to be limited by this particular arrangement. For example, in example embodiments, the first and second engaging members 1700 and 1800 may include protrusions and the third and fourth engaging members 2400 and 2500 may include channels into which the protrusions of the first pair of engaging members 1700 and 1800 may be inserted.

Figure 5A:
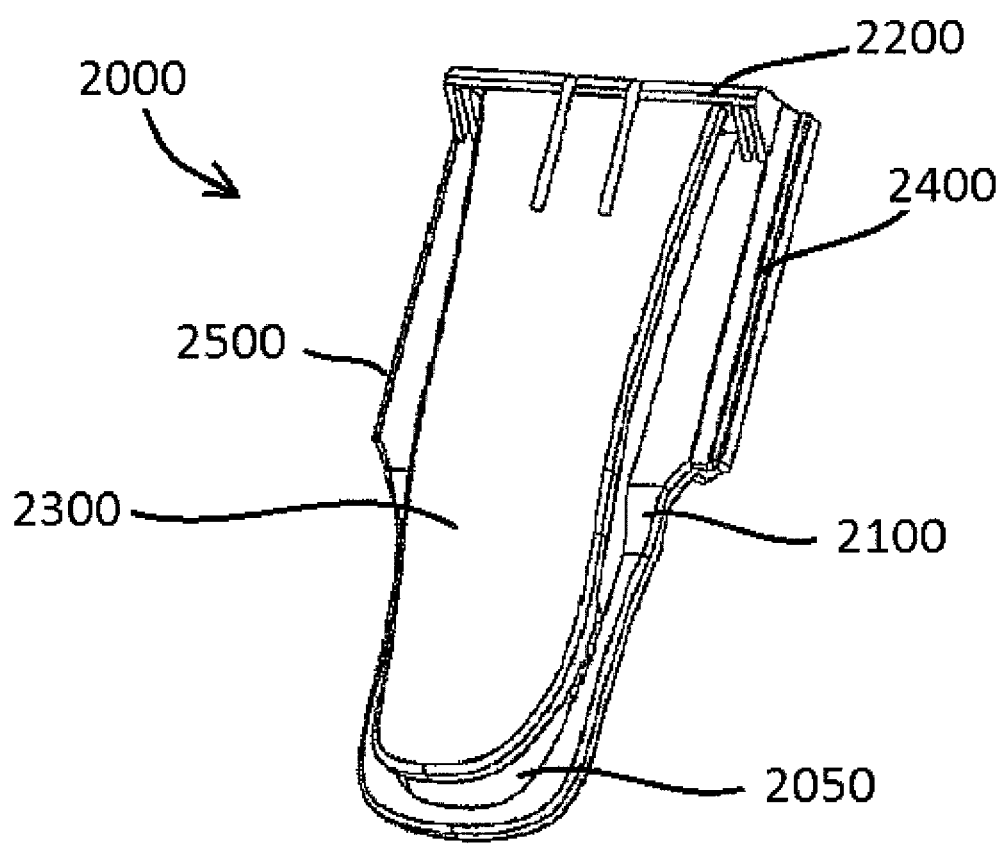
FIGS. 5A-5F are views of a first fastening member in accordance with example embodiments.
Figure 5B:
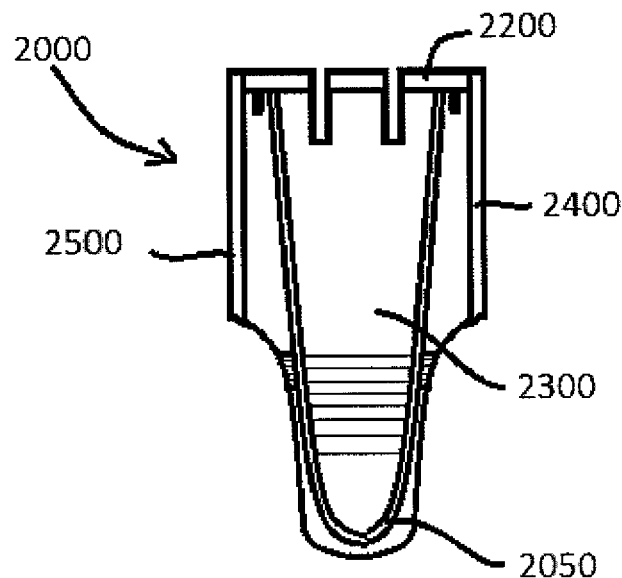
Figure 5C:
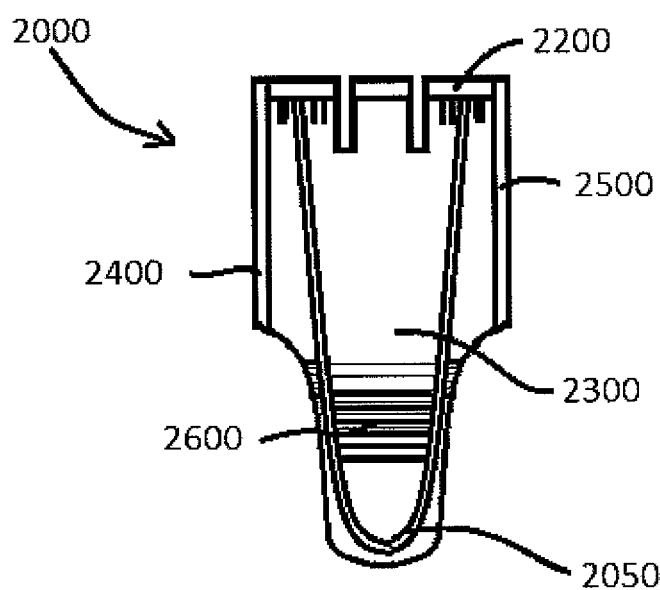
Figure 5D:
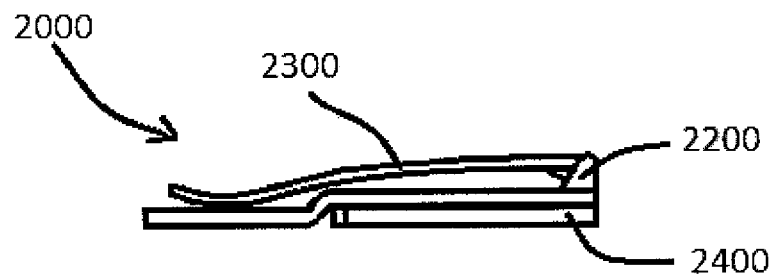
Figure 5E:
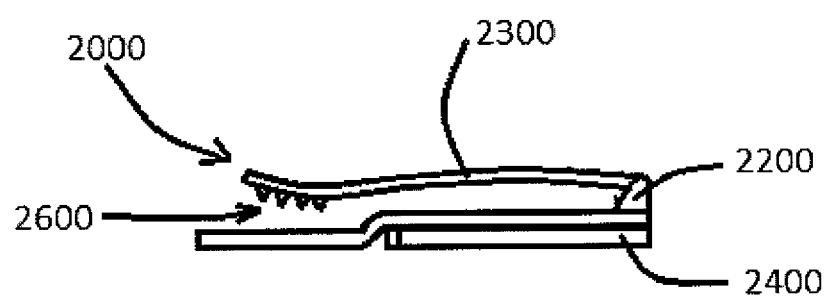
Figure 5F:
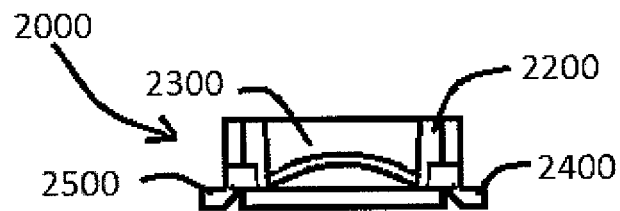

FIGS. 5A-5F illustrate an example of the first fastening member 2000 in accordance with example embodiments. FIG. 5A, for example, is an isometric view of the example first fastening member 2000, FIG. 5B is a top view of the example first fastening member 2000, FIG. 5C is an bottom view of the example first fastening member 2000, FIG. 5D is a side view of the example first fastening member 2000, FIG. 5E is a side view of the example first fastening member 2000 with a tongue 2300 flexed away from a base 2100 of the first fastening member 2000 to show a first protrusion 2600, and FIG. 5F is a front view of the example first fastening member 2000.

Referring to FIGS. 5A-5F, the first fastening member 2000 may include the tongue 2300 attached to a base 2100 by a connecting member 2200. The connecting member 2200 may be a spring loaded member and/or may be a resilient member. For example, the connecting member 2200 may be fabricated from plastic which is elastically deformable. The tongue 2300 may also be formed from a resilient material, for example, plastic. In example embodiments, the tongue 2300 may include the first protrusion 2600 which may be configured to engage a second protrusion 1600 which may be formed on the device 1000 when the third and fourth engaging members 2400 and 2500 are engaged with the first and second engaging members 1700 and 1800. For example, the base 2100 may include an opening 2050 to allow the tongue 2300 having the first protrusion 2600 to press against the second protrusion 1600 such that the first and second protrusions 2600 and 1600 are engaged with one another. Because the tongue 2300 may be a resilient member, the tongue may be flexed away from the second protrusion 1600. In example embodiments, the second protrusion 1600 may include a plurality of ridges which may engage a plurality of ridges formed in the first protrusion 2600. Once the third and fourth engaging members 2400 and 2500 are inserted into the first and second engaging members 1700 and 1800 of the device 1000, the first fastening member 2000 may act as a clip usable for securing the device 1000 to a target, for example, an article of clothing. Accordingly, the first fastening member 2000 may secure the device 1000 to an article of clothing. For example, an article of clothing may be provided between the first and second protrusions 2600 and 1600.

Figure 6A:
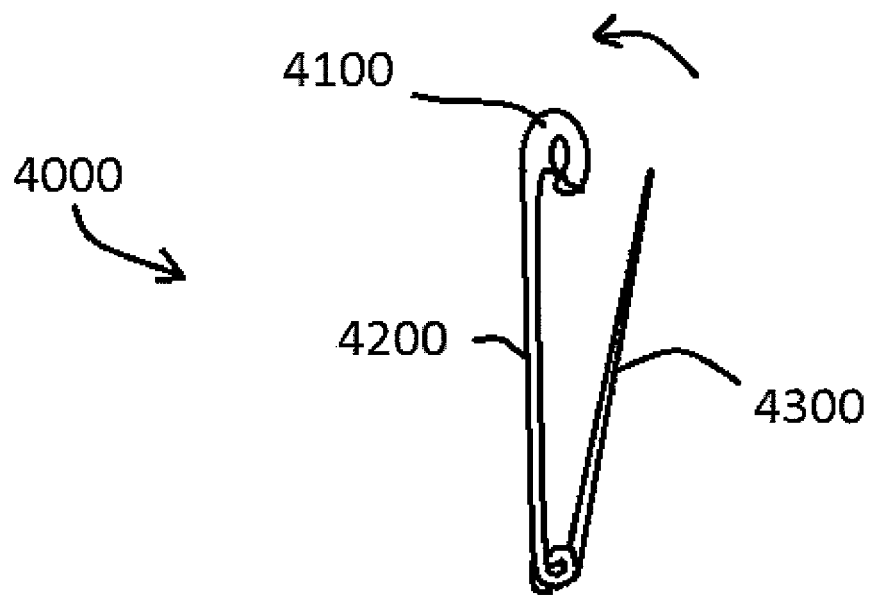
FIGS. 6A-6B are views of a second fastening member in accordance with example embodiments.
Figure 6B:
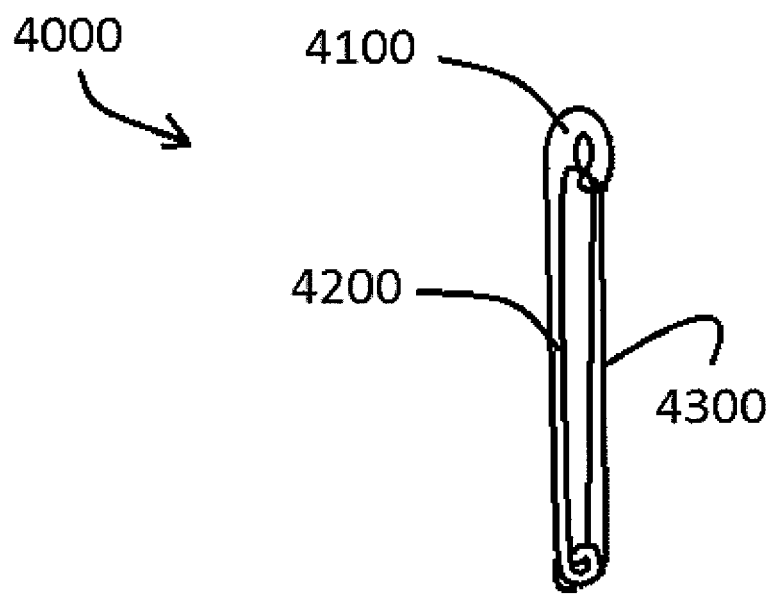

FIGS. 6A and 6B illustrate an example of the second fastening member 4000 in accordance with example embodiments. As shown in FIGS. 6A and 6B, the second fastening member 4000 may be a fastener, for example, a safety pin. Although safety pins are well known in the art, a brief description thereof is provided for the sake of completeness. As shown in FIGS. 6A and 6B, the second fastening member 4000 may include a head 4100, a body 4200, and an end 4300. As is well known in the art, the body 4200 and the end 4300 may be comprised of a wire which may be bent to form a loop at one end and which may be flexed so as to be in a closed position as shown in FIG. 6B where the end 4300 is captured by the head 4100. In FIG. 6A, the second fastening member 4000 is shown in an open position.

Figure 7:
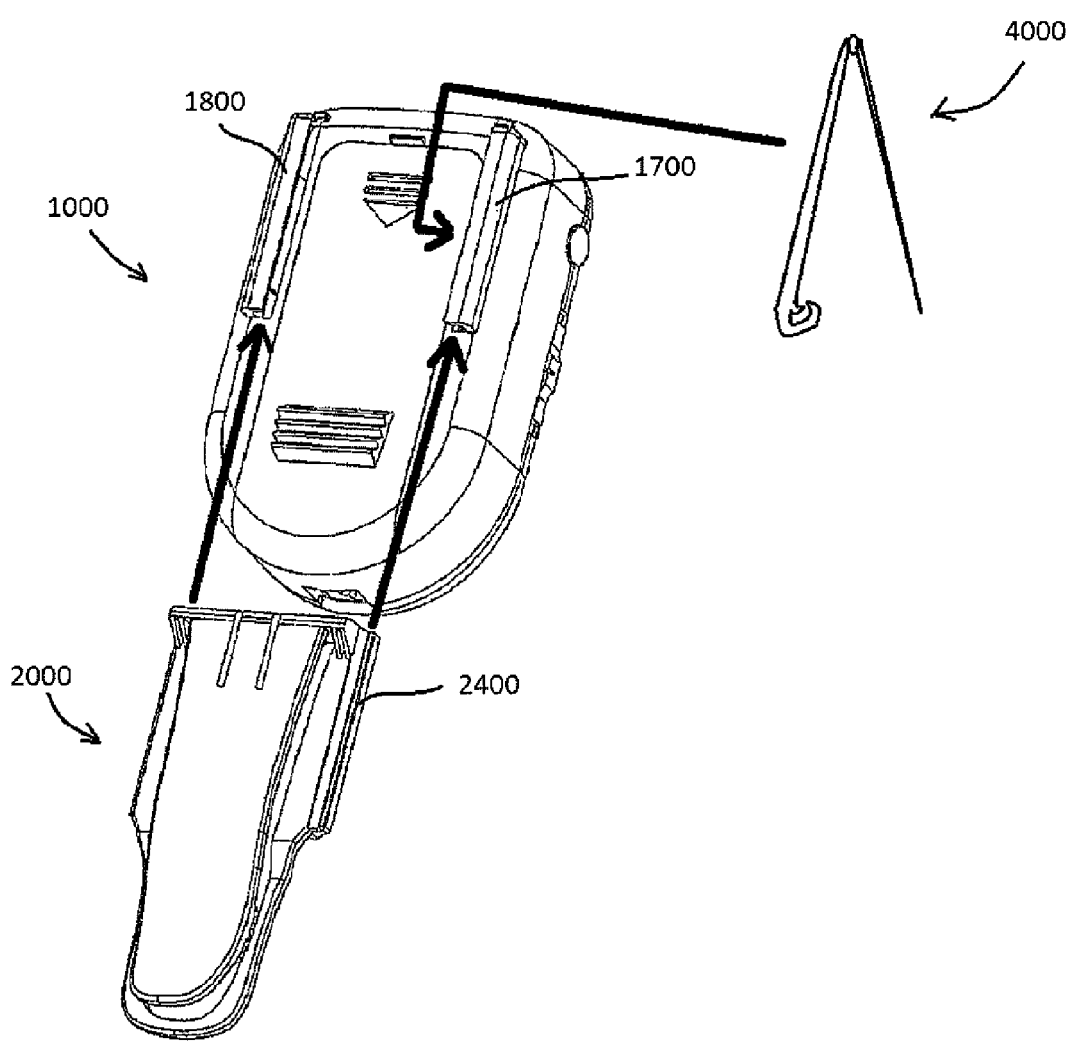
FIG. 7 is an exploded view of the assembly in accordance with example embodiments and an assembly drawing in accordance with example embodiments.

FIG. 7 illustrates an assembly drawing wherein the device 1000, the first fastening member 2000, and second fastening member 4000 are assembled. As shown in FIG. 7, at least a portion of the second fastening member 4000, for example, the body 4200, may be inserted into the first engaging member 1700. More specifically, the body 4200 of the second fastening member 4000 may be inserted into a channel of the first engaging member 1700. After the body 4200 of the second fastening member 4000 is inserted into the channel of the first engaging member 1700, the first fastening member 2000 may be moved so that the third and fourth engaging members 2400 and 2500 of the first fastening member 2000 are inserted into the channels of the first and second engaging members 1700 and 1800. After the engaging members 2400 and 2500 of the second member 2000 are inserted into the engaging members 1700 and 1800 of the device 1000, the second fastening member 4000 is locked in place since the head 4100 and end 4300 of the second fastening member 4000 prevents the second fastening member 4000 from traversing through the channel.

Figure 8A:
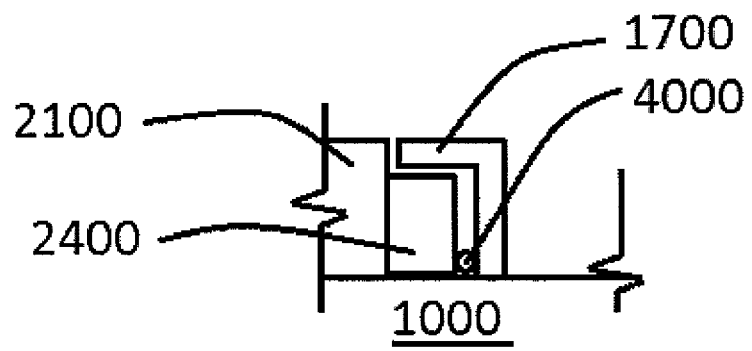
FIGS. 8A-8F are views of engaging members of the device and the first fastening member capturing the second fastening member in place in accordance with example embodiments.
Figure 8B:
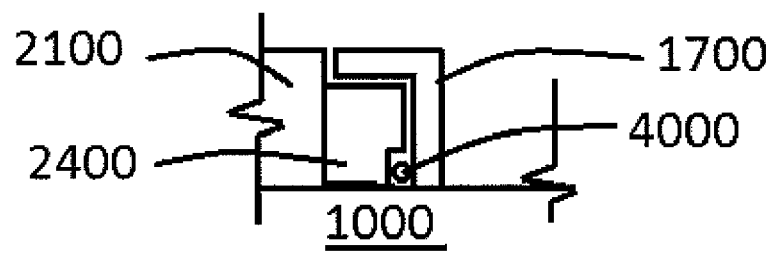
Figure 8C:
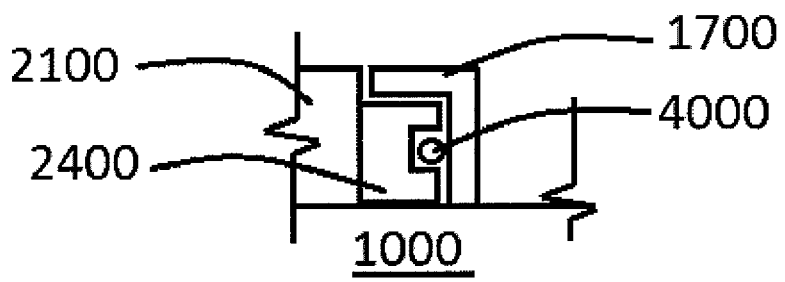
Figure 8D:
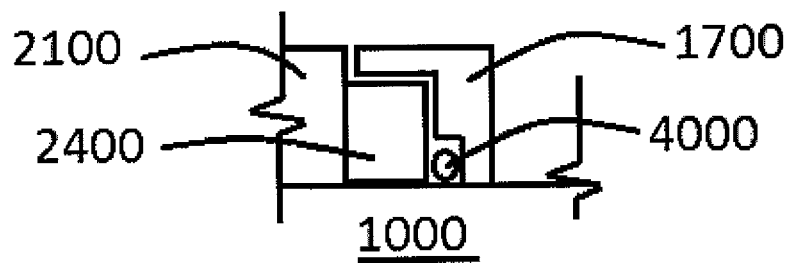
Figure 8E:
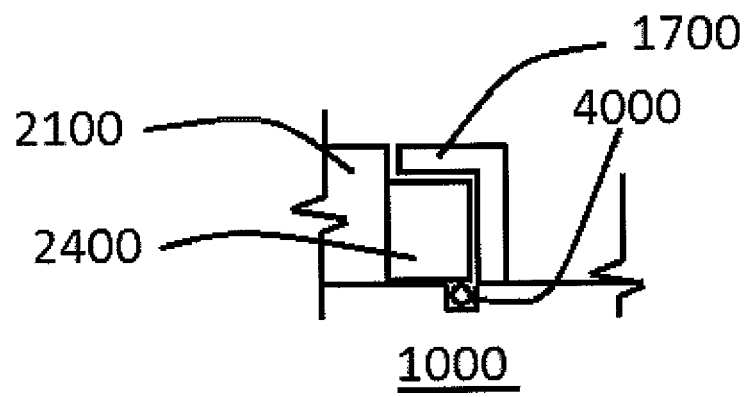
Figure 8F:
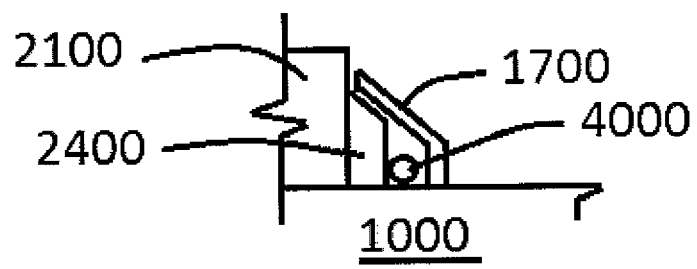

FIGS. 8A-8F illustrate various examples of the third engaging member 2400 engaged with the first engaging member 1700. For example, in FIG. 8A, the first and third engaging members 1700 and 2400 may be configured so that a gap between them accommodates the body 4200 second fastening member 4000 as shown in FIG. 8A. In the alternative, the third engaging member 2400 may be formed with a step that accommodates body 4200 of the second fastening member 4000 as shown in FIG. 8B. Further yet, the third engaging member 2400 may be formed with a groove to accommodate the body 4200 of the second fastening member 4000 as shown in FIG. 8C. Further yet, the first engaging member 1700 may be configured with a groove that accommodates the body 4200 of the second fastening member 4000 as shown in FIG. 8D. Further yet, the first member 1000 may be configured with a groove that accommodates the body 4200 of the second fastening member 4000 as shown in FIG. 8E. Further yet, each of the first engaging member 1700 and the third engaging member 2400 may be configured with an inclined surface as shown in FIG. 8F. Although a gap is illustrated as being between the inclined surfaces of the first engaging member 1700 and the third engaging member 2400, first engaging member 1700 and the third engaging member 2400 may be contacting each other such that no gap is present between them. In example embodiments, the body 4200 may be captured between the first engaging member 1700 and the third engaging member 2400 as shown in FIG. 8F.

Example embodiments provide a device 1000 wherein a second fastening member 4000 is locked into place by engaging members 1700 and 1800 of the device 1000 and the engaging members of the first fastening member 2000. The device 1000 may be, but is not limited to, an electronic device such as an alarm for a urine detection system, a cell phone, or a paging device. The first fastening member 2000 may include a tongue 2300 that may engage a surface of the device 1000 and thus may act as a clip which may be usable for attaching the device 1000 to a target, for example, an article of clothing. The second fastening member 4000 may be a fastener, for example, a safety pin. Thus, the second fastening member 4000 is also usable for attaching the device 1000 to the target. For example, in the event the target is a shirt without a pocket, the second fastening member 4000 may be used to attach the device 1000 to the shirt.

The figures and the above description are merely exemplary and are not intended to limit the invention. For example, although the device 1000 has been described as an electronic device that may be configured to connect to a detector by a cable, example embodiments are not limited thereto. For example, the device 1000 may be an electronic device which is wirelessly connected to the detector. Furthermore, as indicated above, the device 1000 may be another type of electronic device such as a cell phone, a pager, or a recording device. Thus, the electronic device 1000 is not required to have a power button 1100, switch 1200, speaker 1400, or port 1300. In addition, the device 1000 is not required to be an electronic device.

Although not shown in the figures, it is understood that a third fastening member may be incorporated. For example, the third fastening member may resemble a safety pin that is captured by the second and fourth engaging member 1800 and 2500 in a manner similar to the second fastening member 4000 being captured by the first and third engaging members 1700 and 2400.

While example embodiments have been particularly shown and described with reference to example embodiments thereof, it will be understood by those of ordinary skill in the art that various changes in form and details may be made therein without departing from the spirit and scope of the invention.

What I claim is:

1. An assembly comprising:
   a first engaging member on a device;
   a second engaging member engaging the first engaging member; and
   a first fastener configured to attach the device to a target, wherein
   the first fastener is captured by the first engaging member and the second engaging member,
   the first engaging member is one of a protrusion and a sleeve and the second engaging member is the other of the protrusion and the sleeve,
   the sleeve includes a channel into which the protrusion and at least a portion of the first fastener is inserted,
   the second engaging member is part of a second fastener,
   the second fastener is a clip, and
   the first fastener is a safety pin.

2. The assembly according to claim 1, wherein the second engaging member is the protrusion and the first engaging member is the sleeve having a channel in which the protrusion and at least a portion of the first fastener is inserted.

3. An assembly comprising:
   a first engaging member on a device;
   a second engaging member engaging the first engaging member; and
   a first fastener configured to attach the device to a target, wherein
   the first fastener is captured by the first engaging member and the second engaging member,
   the second engaging member is a protrusion and the first engaging member is a sleeve having a channel in which the protrusion and at least a portion of the first fastener is inserted, and
   the protrusion includes at least one of a groove and a step into which a portion of the first fastener is inserted.

4. An assembly comprising:
   a first engaging member on a device;
   a second engaging member engaging the first engaging member; and
   a first fastener configured to attach the device to a target, wherein
   the first fastener is captured by the first engaging member and the second engaging member,
   the second engaging member is a protrusion and the first engaging member is a sleeve having a channel in which the protrusion and at least a portion of the first fastener is inserted, and
   the first engaging member includes a groove into which at least a portion of the first fastener is inserted.

5. An assembly comprising:
a first engaging member on a device;
a second engaging member engaging the first engaging member; and
a first fastener configured to attach the device to a target, wherein
   the first fastener is captured by the first engaging member and the second engaging member,
   the second engaging member is a protrusion and the first engaging member is a sleeve having a channel in which the protrusion and at least a portion of the first fastener is inserted, and
   the device includes a groove into which a least a portion of the first fastener is inserted.

* * * * *